(12) United States Patent
Natan

(10) Patent No.: US 6,514,767 B1
(45) Date of Patent: Feb. 4, 2003

(54) SURFACE ENHANCED SPECTROSCOPY-ACTIVE COMPOSITE NANOPARTICLES

(75) Inventor: Michael J. Natan, Los Altos, CA (US)

(73) Assignee: SurroMed, Inc., Mountain View, CA (US)

(*) Notice: Subject to any disclaimer, the term of this patent is extended or adjusted under 35 U.S.C. 154(b) by 96 days.

(21) Appl. No.: 09/680,782

(22) Filed: Oct. 6, 2000

Related U.S. Application Data
(60) Provisional application No. 60/157,931, filed on Oct. 6, 1999, and provisional application No. 60/190,395, filed on Mar. 17, 2000.

(51) Int. Cl.$^7$ .............................................. G01N 21/75

(52) U.S. Cl. ........................... 436/166; 436/56; 436/73; 436/80; 436/525; 422/82.05; 422/82.09; 356/301

(58) Field of Search ............................... 436/56, 73, 80, 436/164, 166, 525, 805; 422/82.05, 82.09; 250/458.1, 459.1; 356/300, 301

(56) References Cited

U.S. PATENT DOCUMENTS

| | | | |
|---|---|---|---|
| 5,023,139 A | 6/1991 | Birnboim et al. | |
| 5,266,498 A | 11/1993 | Tarcha et al. | |
| 5,609,907 A | 3/1997 | Natan | |
| 5,825,790 A | 10/1998 | Lawandy | |
| 5,828,450 A | 10/1998 | Dou et al. | |
| 6,149,868 A | 11/2000 | Natan et al. | |
| 6,219,137 B1 * | 4/2001 | Vo-Dinh | 356/301 |

FOREIGN PATENT DOCUMENTS

| WO | WO 99/21934 | 5/1999 |
|---|---|---|

OTHER PUBLICATIONS

Akbarian et al. "Porous sol–gel silicates containing gold particels as matrixes for surface–enhanced Raman spectroscopy", J. Raman Spectr., 1996, v. 26, No 10, pp. 775–783.*
Shibata et al. "Preparation of Silica Microspheres Containing Ag Nanoparticles", J. Sol–Gel technol., 1998, v. 11, pp. 279–287.*
Felidj et al. "A new approach to determine nanoparticle shape and size distributions of SERS–active gold–silver mixed colloids", New J. Chem., 1998, pp. 725–732.*
Freeman et al. "Ag–clad Au nanoparticles: novel aggregation, optical. An D surface–enhanced Raman scattering properties", J. Phys. Chem., 1996, v. 100, pp. 718–724.*
U.S. patent application Ser. No. 09/378,259, Dietz et al., filed Aug. 20, 1999.
U.S. patent application Ser. No. 09/558,094, Dietz et al., filed Apr. 26, 2000.
Chan et al. (1998) Science 281:2016–2018.
Emory et al. (1997) Analytical Chemistry 69:2631–2635.
Emory et al. (1998) J. Phys Chem. B 102:493–497.
Emory et al. (1998) J. American Chemical Society 120:8009–8010.
Grabar et al. (1995) Analytical Chemistry 67:735–743.
Kneipp et al. (1998) Exp. Techn. Phys. 36 2:161–166.
Kneipp et al. (1995) Applied Spectroscopy 49:780–784.
Kneipp et al. (1996) Phys. Rev. Letters 76:2444–2447.
Kneipp et al. (1997) Phys. Rev. Letters 78:1667–1670.
Kneipp et al. (1998) Applied Spectroscopy 52:175–178.
Kneipp et al. (1998) Applied Spectroscopy 52:1493–1497.
Kneipp et al. (1998) Phys. Rev. E 57:6281–6284.

(List continued on next page.)

Primary Examiner—Jill Warden
Assistant Examiner—Yelena Gakh
(74) Attorney, Agent, or Firm—Swanson & Bratschun, L.L.C.

(57) ABSTRACT

Metal nanoparticles associated with a spectroscopy-active analyte and surrounded by an encapsulant are useful as sensitive optical tags detectable by surface-enhanced spectroscopy.

24 Claims, 4 Drawing Sheets

OTHER PUBLICATIONS

Kneipp et al. (1999) Chem. Review 99:2957–2975.
Kneipp et al. (1999) Current Science 77:915–924.
Lyon et al. (1997) Anal. Chem. 69:3400–3405.
Nie et al. (1997) Science 275:1102–1106.
Nie et al. (1997) Annu. Rev. Biophys. Biomol. Struct. 26:567–596.
Stober et al. (1968) J. Colloid Interface Sci. 26:62–69.
Ung et al. (1998) Langmuir 14:3740–3748.
Van Duyne et al. (1993) J. Chem Phys. 99:2101–2115.

* cited by examiner

SURFACE ENHANCED SPECTROSCOPY-ACTIVE COMPOSITE NANOPARTICLES

RELATED APPLICATIONS

This application claims priority to U.S. Provisional Application No. 60/157,931 filed Oct. 6, 1999, entitled "Glass Coated Surface Enhanced Raman Scattering Tags", and U.S. Provisional Application No. 60/190,395, filed Mar. 17, 2000, entitled "GANS Particles."

FIELD OF THE INVENTION

The invention is directed to surface enhanced spectroscopy-active composite nanoparticles, methods of manufacture of the particles, and uses of the particles (including their use as molecular or cellular optical tags). More particularly, it is directed to the area of submicron-sized tags or labels that can be covalently or non-covalently affixed to entities of interest for the purpose of quantitation, location, identification, and/or tracking.

BACKGROUND OF THE INVENTION

When light is directed onto a molecule, the vast majority of the incident photons are elastically scattered without a change in frequency. This is termed Rayleigh scattering. However, the energy of some of the incident photons (approximately 1 in every $10^7$ incident photons) is coupled into distinct vibrational modes of the molecule's bonds. Such coupling causes some of the incident light to be inelastically scattered by the molecule with a range of frequencies that differ from the range of the incident light. This is termed the Raman effect. By plotting the frequency of such inelastically scattered light against its intensity, the unique Raman spectrum of the molecule under observation is obtained. Analysis of the Raman spectrum of an unknown sample can yield information about the sample's molecular composition.

The incident illumination for Raman spectroscopy, usually provided by a laser, can be concentrated to a small spot if the spectroscope is built with the configuration of a microscope. Since the Raman signal scales linearly with laser power, light intensity at the sample can be very high in order to optimize sensitivity of the instrument. Moreover, because the Raman response of a molecule occurs essentially instantaneously (without any long-lived highly energetic intermediate states), photobleaching of the Raman-active molecule—even by this high intensity light—is impossible. This places Raman spectroscopy in stark contrast to fluorescence spectroscopy, where photobleaching dramatically limits many applications.

The Raman effect can be significantly enhanced by bringing the Raman-active molecule(s) close (<50 Å) to a structured metal surface; this field decays exponentially away from the surface. Bringing molecules in close proximity to metal surfaces is typically achieved through adsorption of the Raman-active molecule onto suitably roughened gold, silver or copper or other free electron metals. Surface-enhancement of the Raman activity is observed with metal colloidal particles, metal films on dielectric substrates, and with metal particle arrays. The mechanism by which this surface-enhanced Raman scattering (SERS) occurs is understood, and is thought to result from a combination of (i) surface plasmon resonances in the metal that enhance the local intensity of the light, and; (ii) formation and subsequent transitions of charge-transfer complexes between the metal surface and the Raman-active molecule.

SERS allows detection of molecules attached to the surface of a single gold or silver nanoparticle. A Raman enhancing metal that has associated or bound to it a Raman-active molecule(s) is referred to as a SERS-active nanoparticle. Such SERS-active nanoparticles can have utility as optical tags. For example, SERS-active nanoparticles can be used in immunoassays when conjugated to an antibody against a target molecule of interest. If the target of interest is immobilized on a solid support, then the interaction between a single target molecule and a single nanoparticle-bound antibody could be detected by searching for the Raman-active molecule's unique Raman spectrum. Furthermore, because a single Raman spectrum (from 100 to 3500 $cm^{-1}$) can detect many different Raman-active molecules, SERS-active nanoparticles may be used in multiplexed assay formats.

SERS-active nanoparticles offer the potential for unprecedented sensitivity, stability, and multiplexing functionality, when used as optical tags in chemical assays. However, SERS-active nanoparticles made from metals present formidable practical problems when used in such assays. Metal nanoparticles are exceedingly sensitive to aggregation in aqueous solution; once aggregated, it is not possible to re-disperse them. In addition, the chemical compositions of some Raman-active molecules are incompatible with the chemistries used to attach other molecules (such as proteins) to metal nanoparticles. This restricts the choices of Raman-active molecules, attachment chemistries, and other molecules to be attached to the metal nanoparticle.

The most significant problem with the use of metal nanoparticles as Raman tags is the similarity of the Raman spectra of molecules to be coupled to the nanoparticles. For example, in a multiplexed sandwich immunoassay, the Raman spectra of the secondary antibodies to which the nanoparticles are attached would be highly similar, and thus impossible to deconvolute. Moreover, the parts of the secondary antibodies that are different, i.e., the antigen-binding domains, are typically too far away from the metal surface to be significantly enhanced.

The prior art teaches that molecules themselves can be used as Raman tags, provided that their Raman scattering cross section is sufficiently large. Thus, direct attachment of dyes, for example, to antibodies, allows them to be used as tags for immunoassays. This approach, however, suffers from extremely significant limitations: the molecular structures/features that give rise to intense Raman spectra (e.g. polarizability, aromaticity, conjugation, heteroatoms, and most significantly, significant absorption cross section) also give rise to complex Raman spectra. The use of molecular Raman tags requires very high extinctions in the visible region of the spectrum to access resonance Raman scattering, which increases the Raman signal by up to three orders of magnitude. There is a fundamental physical incompatibility between molecules that absorb visible light well and those that exhibit simple Raman spectra. Thus, the Raman spectra of the dyes described above are exceedingly complex, and it has not been possible to multiplex these assays.

A second fundamental problem with Raman-based tags is the weakness of the Raman signal; it is not possible to detect single molecules (or even thousands of molecules) by Raman without using surface enhancement. Ideally, one would like a tag that exhibits the enhancement factors associated with SERS and the ability to attach such a tag to a freely diffusing species (which would clearly not be possible with macroscopic SERS-active surfaces).

It is an object of this invention to provide a solution to the abovementioned problems encountered when using Raman scattering entities as optically-addressable labels or tags, especially in chemical or biomolecular assays. It is a further object of the invention to provide a panel of at least 20 different SERS-active nanoparticles for use as "cleaveless" optical tags in bead-based combinatorial chemical syntheses. It is a further object of this invention to describe an optical detection system for multiplexed assays.

The present invention is directed to surface enhanced spectroscopy-active composite nanoparticles, including SERS-active composite nanoparticles (SACNs). Also included within the scope of this invention are methods of manufacture of the particles, and uses of the particles (including their use as molecular or cellular optical tags). The submicron-sized-tags or labels of the invention can be covalently or non-covalently affixed to entities of interest (that may range in size from molecules to macroscopic objects) for the purpose of quantitation, location, identification, and/or tracking.

SUMMARY OF THE INVENTION

The present invention overcomes the problems encountered when using a spectroscopy-active species, such as a Raman scattering species, as an optical tag. The invention provides novel SES-active composite nanoparticles, including SERS-active composite nanoparticles (SACNs). Such nanoparticles each comprise a SES-active metal nanoparticle, a submonolayer, monolayer, or multilayer of spectroscopy-active species in close proximity to the metal surface, and an encapsulating shell comprising a polymer, glass, or any other dielectric material. This places the spectroscopy-active molecule (alternately referred to herein as the "analyte"; not to be confused with the species in solution that is ultimately being quantified) at the interface between the metal nanoparticle and the encapsulant.

In preferred embodiments, the encapsulant is glass. The resulting glass-coated analyte-loaded nanoparticles (GANs) retain the activity of the SES-active metal nanoparticles, but tightly sequester this activity from the exterior surface of the nanoparticle. Thus, in the case of surface active Raman scattering (SERS), the resulting GANs exhibits SERS activity, but the Raman-active analyte is located at the interface between the metal nanoparticle and the encapsulant.

The analyte molecule can be chosen to exhibit extremely simple Raman spectra, because there is no need for the species to absorb visible light. This, in turn, allows multiple GANs particles, each with different analyte molecules, to be fabricated such that the Raman spectrum of each analyte can be distinguished in a mixture of different types of GANs particles.

GANs are easily handled and stored. They are also aggregation resistant, stabilized against decomposition of the analyte in solvent and air, chemically inert, and can be centrifuged and redispersed without loss of SERS activity.

Most importantly, the glass shells of GANs may be readily derivatized by standard techniques. This allows GANs to be conjugated to molecules (including biomolecules such as proteins and nucleic acids) or to solid supports without interfering with the Raman activity of the GANs. Unlike metal nanoparticles, GANs can be evaporated to dryness, and then completely redispersed in solvent. Using the techniques provided herein, it is possible to fabricate GANs that are individually detectable using SERS.

The SACNs provided by the present invention are uniquely identifiable nanoparticles. They can be used in virtually any situation in which it is necessary to label molecules or objects (including beads and other types of solid support), with an optical tag. Biomolecules can be conjugated readily to the exterior of SACNs by standard techniques, thereby allowing the particles to function as optical tags in biological assays. SACNs can be used in virtually any assay that uses an optical tag, such as a fluorescent label. However, as optical tags, SACNs have several distinct advantages over fluorescent labels. These advantages include vastly more sensitive detection, chemical uniformity, and the absolute resistance of the SERS activity to photobleaching or photodegradation. A further benefit of using SACNs as optical tags is the ease with which individual SACNs having different SERS-activities may be resolved from one another. At least twenty different SACNs are resolvable from one another using a simple Raman spectroscope. This enables multiplexed assays to be performed using a panel of different SACNs, each having a unique and distinguishable SERS-activity.

In addition, SACNs can serve as novel "cleaveless" optical tags in bead-based combinatorial chemical syntheses. In this embodiment, each synthetic step in the scheme can be accompanied by the conjugation of a unique SACN to the bead. The reaction history of the bead, and hence the identity of the synthesized compound, can then be determined by reading the SERS spectrum of the bead, without first requiring that the SACNs are cleaved from the bead.

DETAILED DESCRIPTION OF THE PREFERRED EMBODIMENTS

Figure 1A:
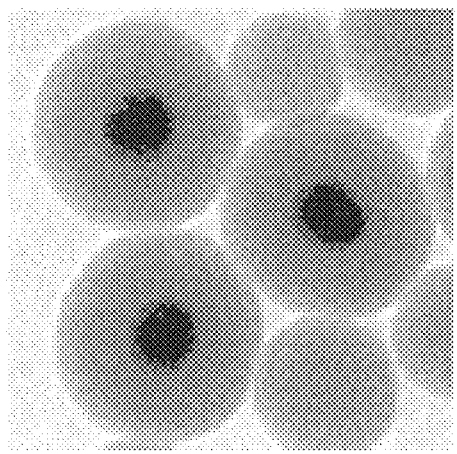
FIG. 1A shows transmission electron microscopes of GANs comprising 35 nm Au cores with 40 nm glass.

The present invention is directed to surface enhanced spectroscopy-active composite nanoparticles, including SERS-active composite nanoparticles (SACNs). Also included within the scope of this invention are methods of manufacture of the particles, and uses of the particles (including their use as molecular or cellular optical tags). The submicron-sized tags or labels of the invention can be covalently or non-covalently affixed to entities of interest (that may range in size from molecules to macroscopic objects) for the purpose of quantitation, location, identification, and/or tracking.

Preferred Embodiments

SERS-active composite nanoparticles (SACNs) are comprised of a metal nanoparticle that has attached or associated with its surface one or more Raman-active molecules (alternately referred to herein as "analytes"). This complex of Raman enhancing metal and analyte (referred to as a SERS-active metal nanoparticle) is then coated or encapsulated by an encapsulant. In preferred embodiments, the encapsulant is a glass material, and the SACN is referred to then as a glass-coated analyte loaded nanoparticle (GAN).

In preferred embodiments, SACNs are provided by growing or otherwise placing a shell of a suitable encapsulant over a SERS-active metal nanoparticle core. The metal nanoparticle core is preferably a gold or silver sphere of 20–200 nm in diameter. Most preferred is an oblate or prolate metal spheroid of the same materials. For SERS using red incident light (~633 nm), the optimal SERS response is obtained with 63 nm diameter gold nanoparticle cores. Metal nanoparticles of the desired size can be grown as metal colloids by a number of techniques well known in the art. For example, chemical or photochemical reduction of metal ions in solution using any number of reducing agents has been described. Likewise, nanoparticle syntheses have been carried out in constrained volumes, e.g. inside a vesicle. Nanoparticles can be made via electrical discharge in solution. Dozens of other methods have been described, dating back to the mid-1800's.

Preferably, the encapsulant does not measurably alter the SERS activity of the metal nanoparticle. However the advantages of the present invention are still achieved even if the encapsulant has some measurable effect, provided it does not interfere with the SERS activity, or does not add significant complexity to the Raman spectrum. In addition, the encapsulant should be readily modified in order to attach molecules, including biomolecules, to its exterior surface. Suitable encapsulants include, but are not limited to, glass, polymers, metals, metal oxides (such as $TiO_2$ and $SnO_2$), and metal sulfides. The encapsulation is carried out after, or during, adsorption to the core nanoparticle of the Raman-active analyte that is to provide the SERS activity of the SACN. In this way, the Raman-active analyte is sequestered from the surrounding solvent as a coating on the surface of the metal nanoparticle core. Such a configuration provides the metal nanoparticle core with stable SERS activity. A Raman-active analyte can form a sub-monolayer, a complete monolayer, or a multilayer assembly on the surface of the metal nanoparticle core. A Raman-active analyte can comprise a single species of Raman-active molecule, or it can be a mixture of different species of Raman-active molecules.

In especially preferred embodiments, the encapsulant is glass (e.g. $SiO_x$). To encapsulate in glass, the metal nanoparticle cores are preferably treated first with a glass primer (that is, a material that can lead to growth of a uniform coating of glass, or can improve adhesion of the glass coat to the particle, or both). Glass is then grown over the metal nanoparticle by standard techniques well known in the art. The resulting SACNs are referred to as glass analyte-loaded nanoparticles (GANs).

Note that glass and many other materials contain functional groups amenable to molecular attachment. For example, immersion of glass in base allows covalent attachment of alkyl trichlorosilanes or alkyl trialkoxysilanes, with additional functionality available on the end of the alkyl group. Thus, glass surfaces can be modified with all forms of biomolecules and biomolecular superstructures including cells, as well as oxides, metals, polymers, etc. Likewise, surfaces of glass can be modified with well-organized monomolecular layers. In short, glass coatings support essentially any and all forms of chemical functionalization (derivatization). This is equally true for many different forms of encapsulant. The point is that SACN particles can be affixed to any species with chemically reactive functionality. All chemical functional groups are reactive under certain conditions. There is thus no limitation to the species that can be immobilized on the encapsulant surface.

The thickness of the encapsulant can be easily varied depending on the physical properties required of the SACN. For example, coatings that are too thick—on the order of 1 micron or more—might preclude obtaining intense Raman spectra. Coatings too thin might lead to interference in the Raman spectrum of the analyte by the molecules on the enscapsulant surface. At the same time, physical properties such as sedimentation coefficient will clearly be affected by the thickness of encapsulant. In general, the thicker the encapsulant, the more effective the sequestration of the Raman-active analyte(s) on the metal nanoparticle core from the surrounding solvent.

For GANs, the preferred glass thickness ranges from 1–40 mn. In some especially preferred embodiments, the GANs comprise 60 nm diameter gold particles encapsulated by a 16 nm thick sphere of glass. The optimization of the dimensions of the SACNs is readily accomplished by one skilled in the art. Accordingly, one might alter the composition of the particle, or its size and shape in accordance with the invention to optimize the intensity of the Raman analyte molecule used as a tag. Indeed, it is known that core-shell nanoparticles (i.e. Au/AuS) support SERS and have very different optical properties compared to pure metal nanoparticles. Likewise, it is known that SERS from prolate spheroids is enhanced relative to spheres with the same major axis. It is further known that single particle enhancements are strongly wavelength-dependent. Thus, one might "tune" the particle size to achieve maximum signal for a given excitation wavelength.

It is often desirable to separate true SACNs from free particles of encapsulant that were not nucleated around a metal nanoparticle. Such separation improves the SERS activity of the nanoparticle preparation because free encapsulant particles are not SERS-active. For example, GANs can be separated from free glass particles by size-exclusion centrifugation in 50% glycerol.

The present invention specifically contemplates the formation of a panel of at least 20 different SACNs, each having a unique SERS spectrum. Because the Raman bands of many molecules are extremely narrow (for example, $CN^-$ is less than 1 nm at FWHM), it is possible to synthesize a panel of SACNs, wherein each contains a Raman analyte that is spaced 20 wavenumbers away in the spectrum from its closest neighbor. For example, a GANs particle with $^{13}CN$ as the analyte is easily distinguished from a GANs with $^{12}CN$ as the analyte, and as well easily distinguishable from one with $C^{15}N$. In this way, it is possible to form 540 distinct and easily resolvable peaks in a single Raman spectrum at 633 nm from 300 to 3000 $cm^{-1}$ using a spectrograph to spread the photons and a CCD camera as a detector. However, practice of the invention is not limited to the above-described instrumentation: Raman experiments with GANs or SACNs can be carried out with visible or near-IR irradiation, make use of Raman bands from 100 $cm^{-1}$ to 5000 $cm^{-1}$, employ any form of monochromator or spectrometer to spatially or temporally resolve photons, and any form of photon detector. This arrangement facilitates the synthesis of panels of at least 10 resolvable SACNs, and provides ample bandwidth for literally hundreds of panels of SACNs.

In order to further increase the ability to distinguish individual SACN populations in the panel from background Raman activity, the invention contemplates the use of Raman-active analytes that have isotopic compositions distinct from naturally abundant species. For example, as described above, $^{13}CN$ is completely resolvable from any natural $^{12}CN$ that may be present in the background. Of course, those skilled in the art will recognize that combinations of isotopes as well as ratios of isotopes can be equally effectively used to identify unique SACNs.

Although the SERS activity of each population of SACNs in the panel is unique, the other properties of the SACNs are kept uniform across the panel. Because the SERS-activity of each SACN is sequestered from the surrounding milieu by the encapsulant, individual populations do not have different solvent or storage requirements. Also, each SACN has the same exterior shell, simplifying the choice of chemistry either for attachment of molecules to the SACNs or attachment of the SACNs to solid supports.

While the examples above have focused on Raman scattering, and in particular surface enhanced Raman scattering as the detection mechanism, a number of analogous methods can apply equally well and are included within the scope of the present invention. For example, one could employ a resonantly-excited analyte, thus making the technique surface enhanced resonance Raman scattering (SERRS). One could also take advantage of published work on enhanced infrared absorption spectra (SEIRA) from nanoscale roughened surfaces. Likewise, Van Duyne and others have shown that surface enhanced hyperRaman scattering (SEHRS) also occurs at nanoscale roughened metal surfaces (as well as the resonant analogue SEHRRS). Note that for a given molecule, with either 3N-5 or 3N-6 unique vibrations, where N is the number of atoms, that all vibrations can be found in either the Raman, hyperRaman, or infrared spectrum. Indeed, identification of certain SACNs could rest on a combination of optical interrogation methods, including SERS, SERRS, SEIRA, SEHRS and SEHRRS.

Note also that a significant amount of (Rayleigh) light scattering is known to occur from particles with dimensions at least 1/10 the exciting wavelength, thus creating the possibility that Rayleigh or hyperRaleigh scattering could be used in identification of SACNs. Moreover, combinations of elastic scattering (e.g. Rayleigh), inelastic scattering (e.g. Raman), and absorption (e.g. IR) could be used to identify particles.

Use of SANCs

The SACNs provided by the present invention can be used in virtually any assay in which a detectable tag or label is required. In some embodiments, SACNs are used in biological and chemical assays as replacements for standard fluorescent tags. Indeed, SACNs possess a number of characteristics that make them far superior to prior art optical tags based on fluorophores. For example, assays using fluorophore detection are commonly hampered by the presence of autofluorescence and other background effects. In addition, many assays require use of a number of different fluorophores; different fluorophores commonly require different attachment chemistries and have different environmental requirements and sensitivities. Particularly noteworthy is the quenching of fluorescent activity that is observed when some fluorophores are conjugated to proteins. Finally, irreversible photodegradation resulting from the creation of a triplet or singlet excited state, followed by a non-reversible chemical reaction that permanently eliminates the excited state—places a severe limitation on the sensitivity of detection. By contrast, SACNs cannot be photobleached or photodegraded, they have uniform chemical and physical properties, and they can be readily resolved from the background. Perhaps most importantly, SACN detection is significantly more sensitive than fluorophore detection. Indeed, it is possible to tag a single molecule with a single SACN, and then detect the presence of that molecule using Raman spectroscopy. Such simple single molecule resolution is without parallel in the fluorophore detection art.

An example of a biological assay in which SACNs can be used as optical tags is the sandwich immunoassay. In sandwich assays, a target to be detected is captured by a solid surface. An antibody (or other ligand) to the same target is attached to a SACN, and then contacted with the solid support. The presence of the SACN SERS signal at the solid support indicates the presence of the antigen. In general, SACNs can be conjugated to any molecule that is used to detect the presence of a specific target in an assay.

In a specifically contemplated embodiment, SACNs are conjugated to nucleic acid molecules. In this way, they can be used in virtually any assay known in the art that detects specific nucleic acid sequences using optically-tagged nucleic acid probes.

SACNs are especially suitable for multiplexed chemical assays in which the identity of SACNs encodes the identity of the target of the assay. Prior art multiplexed assays that use fluorophores to encode target identity are subject to a number of severe constraints imposed by the physical and chemical properties of the fluorophores. Specifically, different fluorophores have different excitation maxima, so coincident excitation of multiple fluorescent tags is not possible. Moreover, fluorescence emission occurs in broad spectral bands, so the bands from one fluorophore often overlap with those of another. As a result, resolving even three different fluorescence activities requires sophisticated optics to separate and then detect the individual emission wavelengths. Because of these problems, multiplexed assays that use fluorophores rely on positional information to reveal target identity. Often, multiplexed assays with fluorophores use a solid support on which ligands are arranged in defined positions. The location of fluorophore signal reveals the identity of the target; the size of the fluorophore signal at that location indicates the amount of the target. However, the synthesis of solid supports with reagents localized at specific positions is expensive and time-consuming. There are limits on the number of features that may be defined on a single surface.

By contrast, the SACNs of the present invention offer remarkable spectral diversity and resolvability. As a result, SACNs can be used in multiplexed assays to yield quantitative and qualitative information without requiring the position-specific localization of reagents. Each SACN coupled to a target-specific reagent can encode the identity of that specific target, and the intensity of a particular Raman signal reveals the quantity of that target. For example, in the sandwich immunoassays described above, the identity of targets captured on the solid support can be determined by using a different flavor of SACN for each target.

Although SACNs are perfectly suited for use in multiplexing applications, they need not be used to encode identity in this manner. They can be used simply as replacements for fluorophores in multiplexed assays in which reagents are localized to specific positions on solid supports. When used in this way, the SACNs offer vastly more sensitive target detection than fluorophores.

Flow cytometry is an example of a multiplexed assay format in which the diversity and resolvability of SACNs can be fully exploited. In one embodiment of this application, populations of beads are provided to which primary antibodies against the targets to be detected are conjugated. The beads are contacted with the assay solution containing the targets, and also with a second set of antibodies against the targets. Each secondary antibody is conjugated to a GAN that encodes the identity of the target to which it will bind. The beads are then passed through a flow cytometer that acquires the Raman spectrum of each bead. Because the Raman spectrometer can sample all frequency space of each bead, it is even possible to place many different primary antibodies on a single bead; the Raman spectrum of each bead can be decoded to determine which SACNs are present and in what quantity; this in turn reveals how much of each target is bound to a single bead. It will be understood that there are many variations of this basic scheme, including the use of reagents other than antibodies to bind to the targets of interest. Accordingly, SACNs can be used in a multitude of variations on this scheme in which it is necessary or useful to tag a reagent.

In preferred embodiments, the SACNs are used as optical tags for Microvolume Laser Scanning Cytometry (MLSC), rather than flow cytometry. MLSC is described in U.S. patent application Ser. No. 09/378,259, filed Aug. 20, 1999, and U.S. patent application Ser. No. 09/558,094, filed Apr. 26, 2000, both incorporated herein by reference in their entirety. In one embodiment of this system, a Raman microscope scans a capillary containing the reagents described above for the flow cytometry applications. The Raman microscope measures the Raman spectrum of each bead in the capillary, thereby obtaining quantitative data for each target to be detected. Again, it is the Raman signal of each SACN that encodes target identity; position specific reagents are not required.

In other embodiments, SACNs are used as optical tags in the solid support-based combinatorial chemical ("combi-chem") synthesis of libraries of novel compounds. One such method is known as "split and pool" synthesis. In this method, a preparation of suitably derivatized resinous beads is randomly divided into multiple populations, and each population is introduced into a different reaction mixture. Different reaction mixtures can contain different reagents, or the same reagents but different reaction conditions. Following reaction, the beads are then washed, recombined and divided again into a set of reaction mixtures. Because of the random manner in which the beads are distributed, each bead will experience a unique reaction history. The result is a bead-based library comprising all of the compounds synthesized using the different permutations of the reaction mixtures. The library may then be screened to identify lead compounds with the desired activity. The lead compounds, in turn, may be analyzed to determine their composition and structure. The combi-chem method has been used to synthesize libraries of peptides, benzodiazapenes, and so on.

If the reaction history of an individual bead is known, then the chemical composition and structure of the compound attached thereto can be determined. There are several ways known in the art for encoding beads with their reaction history. In some methods, each reaction mixture contains a unique identifier molecule that becomes attached to the bead during the reaction step. At the completion of the synthesis, the identifier molecules can be cleaved from the bead of interest, and the reaction history of the bead can be determined by detecting the individual identifier molecules liberated from the bead. For example, prior art methods have used short oligonucleotides to encode reaction histories. These oligomers must be cleaved from the beads, amplified, and then sequenced in order to decode the reaction history; this is a time-consuming process. Because such identifier molecules must first be cleaved from the bead, it is necessary to choose a chemistry in which (a) cleaving the identifier from the bead does not modify or cleave the lead compound from the bead; and/or (b) cleaving the lead compound from the bead does not modify or cleave the identifier molecule. Moreover, the chemistry used to couple the identifier, and often just the presence of the identifier molecules themselves on the surface of the beads, may interfere with the actual combi-chem reactions. Such considerations place considerable restraints on all aspects of the chemistry used in encoded combi-chem synthesis.

The SACNs provided by the present invention can be used to encode the reaction history of beads in such combinatorial schemes. Each reaction mixture can contain a unique species of SACNs, such that each reaction step is accompanied by the attachment of a number of SACNs to the bead upon which the combinatorial synthesis takes place. For example, reaction mixture A can be encoded by $SACN^1$ when used at step 1 in the synthesis scheme, and by $SACN^2$ when used at step 2 in the synthesis scheme, and so on up to $SACN^n$ when used at step n in the synthesis scheme. At the end of the synthesis scheme, the individual beads may be screened for the desired lead compound activity. Beads with the desired lead compound activity are then examined by Raman spectroscopy. The Raman spectrum of each bead is then automatically decoded to detect the individual species of SACNs that have bound to each bead. This information reveals the reaction history of the bead, and hence the structure of the lead compound.

The use of SACNs to encode combi-chem synthesis schemes is a significant advance over the prior art. The entire reaction history of one bead can be determined by taking a single spectral measurement, without requiring that the bead undergo any physical or chemical manipulations. Indeed, the Raman spectrum can even be obtained in microtiter wells. Because the Raman activity of the SACNs can be measured without cleaving them from the bead, the constraints on the choice of chemistries outlined above are greatly reduced. Similarly, the only chemical groupings that the SACNs expose on the surface of the beads are the derivatizing groups that attach the SACN to the bead, and the stable encapsulant. Again, this greatly reduces the problems of identifier molecule interference with the combi-chem synthesis. Finally, the unprecedented spectral diversity offered by the SACNs enables the robust encoding of combi-chem schemes that are far more complex than allowed by prior art encoding methods.

EXAMPLES

Example 1

Synthesis of Glass Analyte-loaded Nanoparticles (GANs)

Materials: Water used for all preparations was 18.2 MΩ, distilled through a Barnstead nanopure system. Snake skin dialysis tubing, 3,500 MWCO, was purchased from Pierce. 3-aminopropyltrimethoxysilane (APTMS), 3-mercaptotrimethoxysilane (MPTMS), and 3-mercaptopropylmethyldimethoxysilane (MPMDMS) were obtained from United Chemical. $HAuCl_4 \cdot 3H_2O$, trisodium citrate dihydrate, sodium hydroxide, trans-1,2-bis(4-pyridyl)ethylene (BPE), pyridine, 2-mercaptopyridine, sodium silicate, tetraethyl orthosilicate (TEOS), and ammonia were obtained from Sigma-Aldrich. BPE was recrystallized several times before use. Dowex cation exchange resin (16–40 mesh) was obtained from J. T. Baker. Pure ethyl alcohol (EtOH) was purchased from Pharmco.

Colloid preparation: 12-nm colloidal Au (nearly spherical, with a standard deviation less than 2 nm) was prepared from $HAuCl_4 \cdot 3H_2O$ reduced by citrate as described in Grabar et al, Analytical Chemistry 67:735–743 (1995), incorporated herein by reference in its entirety. Colloid >12 nm was prepared as follows: 3 ml of 12 mM $HAuCl_4$ was added for every 97 ml of $H_2O$. The solution was then brought to a boil under vigorous stirring and 1 ml of 12-nm Au colloid as a seed and 0.5 ml of 1% sodium citrate per 100 ml of $HAuCl_4$ solution was added and boiled for 10 minutes. The size of the resulting particles was determined by transmission electron microscopy using Gatan or NIH Image software. Finally, the citrate ions surrounding the Au colloid were removed with dialysis, 7 exchanges of at least 4 hours each.

GANs preparation: All reactions were performed in plastic Erylenmeyer flasks. Any amount of colloid could be used in a preparation and the subsequent reactants added in appropriate amounts based on the surface area and concentration of the Au colloid.

A typical experiment used 25 ml of dialyzed, 50-nm, 0.17 nM Au colloid. The pH of the colloid was adjusted from 5 to 7 with the addition of 50 µL of 0.1 M NaOH. The colloid was rendered vitreophilic with the addition 125 µL of 0.5 mM MPTMS (or APTMS, or MPMDMS). After 15 minutes of magnetic stirring, 167 µL of a 0.5 mM solution of the Raman tag (BPE, pyridine, or 2-mercaptopyridine) was added. During another 15 minute period of stirring, a 0.54% solution of active silica was prepared by mixing 1 g of sodium silicate with 50 ml of 3 M NaOH and lowering the pH to 10 with cation exchange resin. One ml of the active silica was added and the resulting solution was approximately pH 9. The solution remained stirring for 15 minutes and then was allowed to stand.

After a 24 hour period, 100 ml of EtOH was added to the solution to proceed with silica growth via the method described in Stöber et al, J. Colloid Interface Sci. 26: 62 (1968), incorporated herein by reference in its entirety. Growth of ~4 nm of additional glass shell was accomplished with the addition of 15 µL of TEOS and 125 µL of ammonia. The reaction was stirred for 15 minutes and then allowed to stand for at least 12 hours. The addition of TEOS and ammonia was continued until the desired shell thickness was obtained.

Example 2

Transmission Electron Microscopy of GANs

Figure 1B:
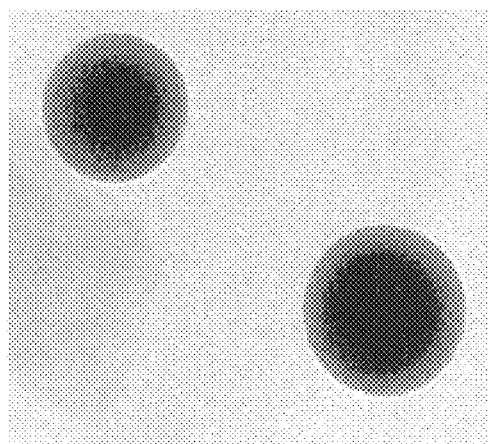
FIG. 1B shows 60 nm Au cores with 16 nm glass.
Figure 2:
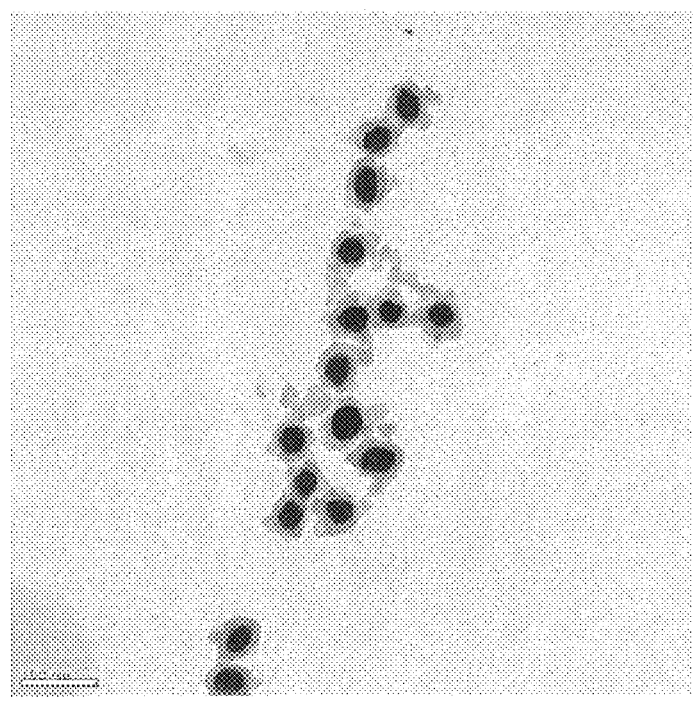
FIG. 2 shows transmission electron micrographs of 35 nm Au, 8 nm glass GANs following centrifugation through a 50% glycerol solution.

Transmission electron microscopy (TEM) images were taken of preparations of GANs; these TEM images illustrate the uniformity of GANs preparations. FIG. 1A shows GANs comprising 35 nm Au cores with 40 nm glass. FIG. 1B shows 60 nm Au cores with 16 nm glass. FIG. 2 illustrates 35 nm Au, 8 nm glass GANs following centrifugation through a 50% glycerol solution.

Example 3

Demonstration of the Sequestration of the Metal Core from Solvent

Figure 3A:
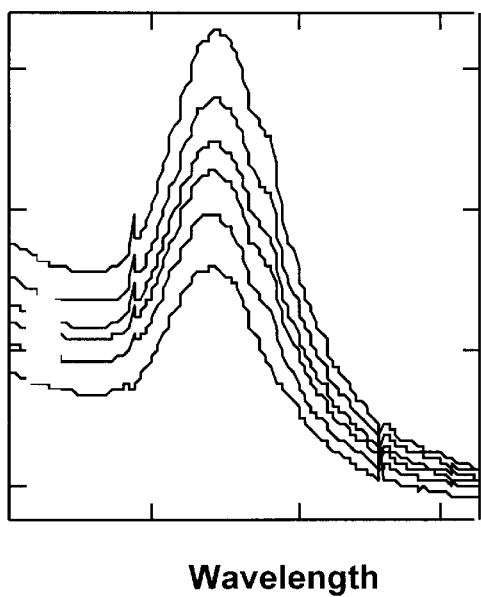
FIG. 3 demonstrates the resistance to acid etching of the gold core of GANs particles with a 35 nm Au core, and 8 nm shell of glass. Etching of the gold core results in a decrease in the absorbance; this is plotted in FIG. 3A (the time after the addition of the etch solution is indicated). The rate of Au etching is shown in FIG. 3B as a plot of absorbance versus time in etch solution.
Figure 3B:
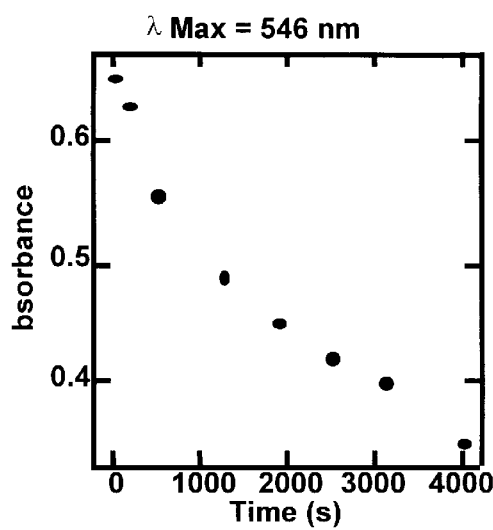

For GANs to function in diverse chemical environment, it is necessary that the Raman-active analyte be sequestered from the surrounding solvent. To demonstrate this sequestration, one may look at diffusion rates through the glass network. This is done by monitoring the rate at which aqua regia (3 $HCl:1HNO_3$) is able to etch out the Au core of a GAN. FIG. 3 demonstrates one such experiment for a batch of GANs particles with a 35 nm Au core, and 8 nm shell of glass. To 500 µl of ≈0.17 nM GANs was added 200 µl of an etch solution (50 µl $HNO_3$ and 150 µl HCl). The absorbance of the solution was measured ($\lambda_{max}$ 546 nm) at various times after addition of the etch solution. Etching of the gold core results in a decrease in the absorbance; this is plotted in FIG. 3A (the time after the addition of the etch solution is indicated). The rate of Au etching is shown in FIG. 3B as a plot of absorbance versus time in etch solution (right). Additional studies performed by the inventors have shown that etching of a Au core by aqua regia does not occur with a 20 nm glass shell over a four hour time period.

Example 4

SERS Spectra of GANs Particles

Figure 4:
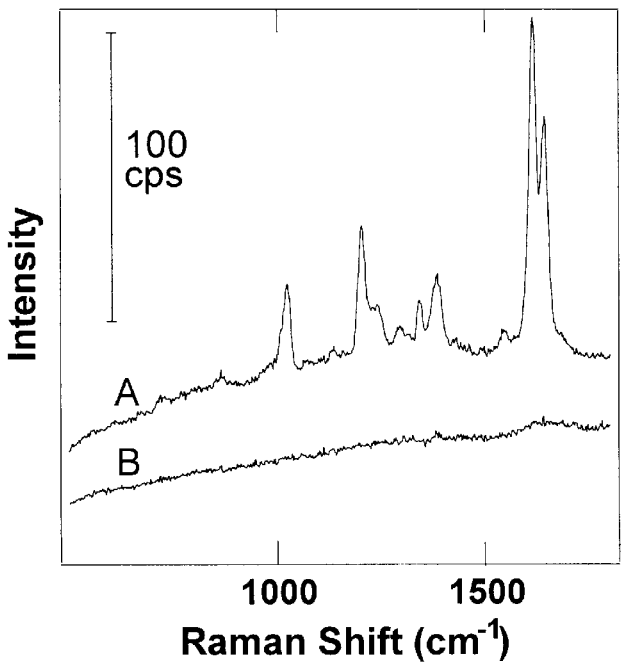
FIG. 4 shows the Raman spectrum of GANs comprising a 40 nm Au core coated with trans-4,4'-bis(pyridyl)ethylene (BPE) encapsulated in 4 nm of glass. Trace A shows the characteristic BPE Raman signal; trace B shows the Raman signal from the same particles without the BPE analyte.

GANs comprising a 40 nm Au core coated with trans-4,4'-bis(pyridyl)ethylene (BPE) encapsulated in 4 nm of glass were synthesized, and examined by Raman spectroscopy. The Raman spectrum obtained using 20 mW of 632.8 nm excitation, with a 3 mm lens and 30 second integration is plotted in FIG. 4. Trace A on the graph shows the characteristic BPE Raman signal; trace B shows the Raman signal from the same particles without the BPE analyte. It can be seen that the GANs without the BPE analyte give essentially no Raman signal.

Example 5

Figure 5:
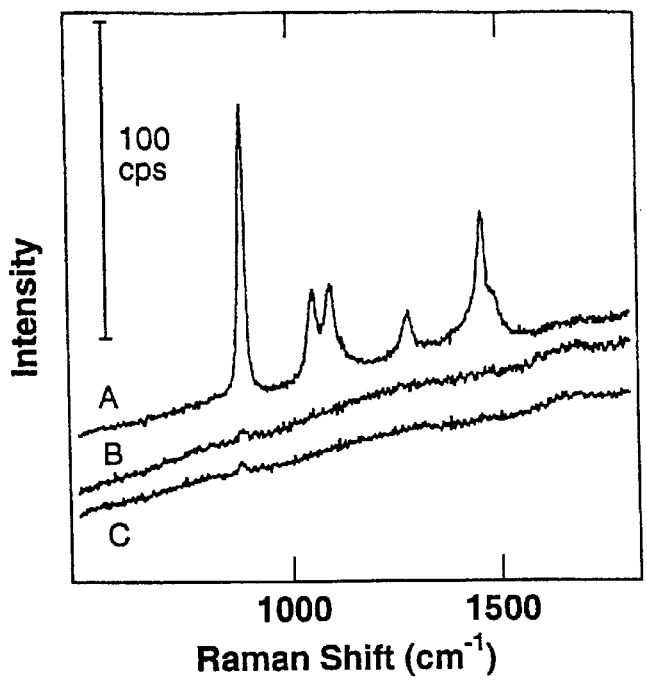
FIG. 5 shows the Raman spectrum of a suspension of GANs comprising 40 nm Au coated with trans-4,4'-bis (pyridyl)ethylene (BPE)/4 nm glass (Trace A); supernatant from a first centrifugation of the GANs (Trace B); and supernatant from a second centrifugation of the GANs (Trace C).

Confinement of the Raman-active Analyte to the Metal Core of GANs by Glass Encapsulation FIG. 5 shows the Raman spectrum of a suspension of GANs comprising 40 nm Au coated with trans-4,4'-bis(pyridyl)ethylene (BPE)/4 nm glass (Trace A); supernatant from a first centrifugation of the GANs (Trace B); and supernatant from a second centrifugation of the GANs (Trace C). It can be seen that the BPE signal does not leave the GAN during each centrifugation step, indicating that the BPE has adhered to the Au core and is tightly sequestered there by glass encapsulation.

Example 6

Figure 6:
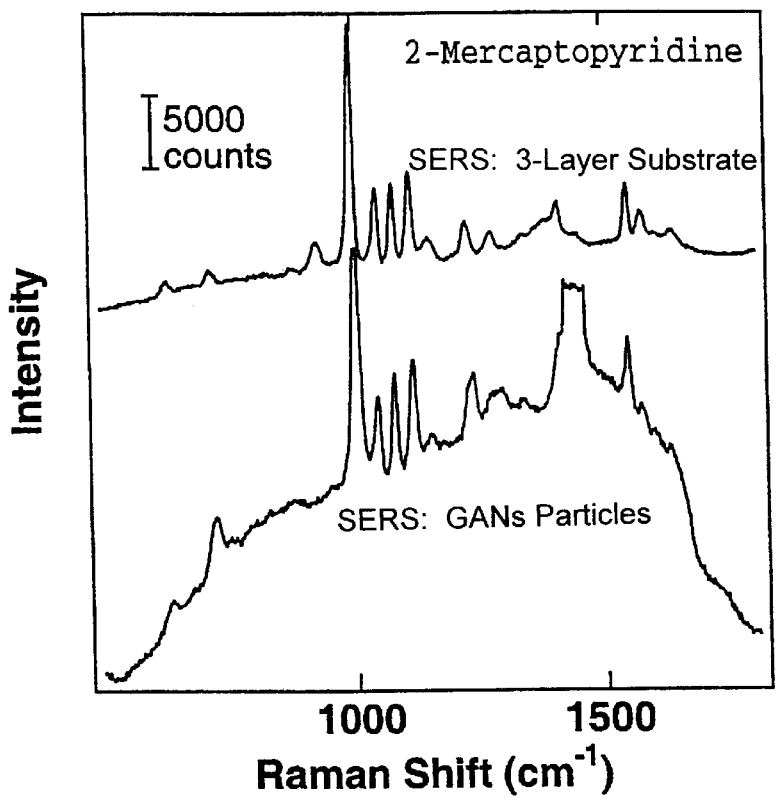
FIG. 6 illustrates the Raman spectra of GANs (80 nm Au core/20 nm glass/2-mercaptopyridine as the analyte ) and of a 50 mM solution of 2-mercaptopyridine absorbed onto a conventional three-layer SERS substrate.

Comparison of SERS Spectra of Raman-active Analytes on GANs with other SERS Substrates GANs (80 nm Au core/20 nm glass) containing 2-mercaptopyridine as the Raman-active analyte were analyzed by Raman spectroscopy using 25 mW of 632.8 nm excitation with a 3 mm lens and 60 seconds of integration. The Raman spectrum of the GAN preparation was then compared with the Raman spectrum obtained when a 50 mM solution of 2-mercaptopyridine is absorbed onto a conventional three-layer SERS substrate (25 mW 632.8 nm excitation, 3 mm lens, 30-seconds integration). FIG. 6 shows the two Raman spectra. It can be seen that the two spectra have identical features and intensities, illustrating that GANs are effective SERS substrates.

Example 7
SERS Spectra of GANs with Mixtures of Raman-active Analytes

Figure 7:
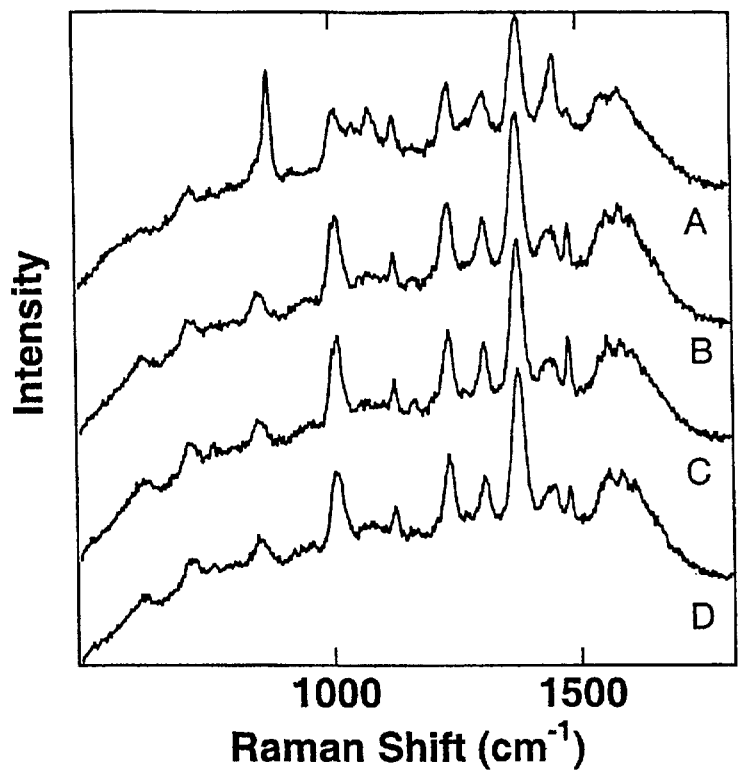
FIG. 7 illustrates the Raman spectra of the following four types ("flavors") of GANs particles: (A) GANs tagged with furonitrile; (B) GANs tagged with furonitrile (66%) and cyanoacetic acid (33%); (B) GANs tagged with furonitrile (33%) and cyanoacetic acid (66%); and (D) GANs tagged with cyanoacetic acid.

SERS spectra of the following four flavors of GANs particles were obtained using 26 mW of 632.8 nm excitation, a 3-mm lens, and 30-second integration: (A) GANs tagged with furonitrile; (B) GANs tagged with furonitrile (66%) and cyanoacetic acid (33%); (B) GANs tagged with furonitrile (33%) and cyanoacetic acid (66%); and (D) GANs tagged with cyanoacetic acid. The percentages indicated are the relative concentrations of each compound in the tagging solution added. FIG. 7 shows that the furonitrile and cyanoacteic acid have relatively the same signal intensity and have similar spectral profiles. The fact that the spectra of B and C are very similar to the spectrum of D indicates that cyanoacetic acid has a better affinity for the Au nanoparticle than furonitrile.

Example 8
SERS Spectra of GANs Tagged with Imidazole (IM) and trans-4,4'-bis(pyridyl)ethylene (BPE)

Figure 8:
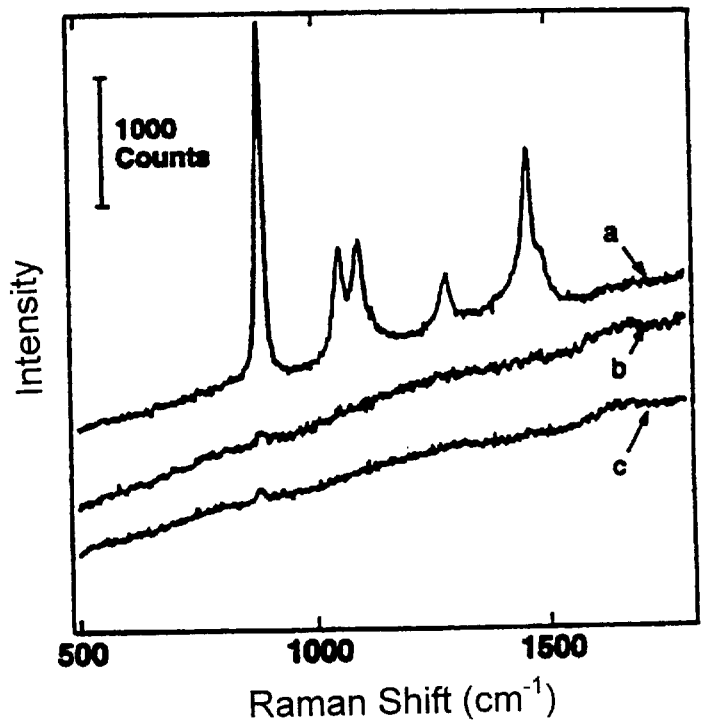
FIG. 8 illustrates the Raman spectra of GANs (40 nm Au core/4 nm glass) (a) tagged with trans-4,4'-bis(pyridyl) ethylene (BPE-GANs) or (b) tagged with imidazole (IM-GANs) or (c) untagged.

GANs (40 nm Au core/4 nm glass) were tagged with either (a) trans-4,4'-bis(pyridyl)ethylene (BPE-GANs) or (b) imidazole (IM-GANs). SERS spectra of these Raman-active analytes are shown in FIG. 8, along with the SERS spectrum of untagged GANs (c) of the same dimensions. BPE-GANs and IM-GANs both show the characteristic Raman bands of their respective Raman-active analytes; untagged GANs do not show these bands.

What is claimed is:

1. A method of tagging a molecule, cell, bead or solid support comprising attaching a particle comprising a surface-enhanced Raman spectroscopy (SERS)-active metal nanoparticle associated with a Raman spectroscopy-active molecule and an encapsulant surrounding said SERS-active metal nanoparticle and said Raman spectroscopy-active molecule to said molecule, cell, bead, or solid support, wherein said particle has a measurable SERS spectrum.

2. The method of claim 1, wherein said metal nanoparticle is comprised of a metal selected from the group consisting of Cu, Na, Al, and Cr.

3. The method of claim 1 wherein said metal nanoparticle is comprised of Au.

4. The method of claim 1 wherein said metal nanoparticle is comprised of Ag.

5. The method of claim 1 wherein said metal nanoparticle is less than 200 nm in diameter.

6. The method of claim 5 wherein said metal nanoparticle has a diameter of 40–100 nm.

7. The method of claim 1 wherein said encapsulant has a thickness of 1–40 nm.

8. The method of claim 7 wherein said encapsulant has a thickness of 3–10 nm.

9. The method of claim 1, wherein said metal nanoparticle comprises a core overlaid with at least one metal shell, and wherein said core and at least one of said metal shells are comprises of a metal selected from the group consisting of Au, Ag, Cu, Na, Al, and Cr.

10. The method of claim 1 wherein said metal nanoparticle comprises an alloy of at least two metals selected from the group consisting of Au, Ag, Cu, Na, Al, and Cr.

11. The method of claim 4, wherein said spectroscopy-active analyte forms a submonolayer coating on said metal nanoparticle.

12. The method of claim 1, wherein said spectroscopy-active analyte forms a monolayer coating on said metal nanoparticle.

13. The method of claim 1, wherein said spectroscopy-active analyte forms a multilayer coating on said metal nanoparticle.

14. The method of claim 11, wherein said encapsulant is selected from the group consisting of glass, polymers, metals, metal oxides, and metal sulfides.

15. The method of claim 1, wherein said encapsulant comprises at least two materials selected from the group consisting of glassed, polymers, metals, metal oxides, and metal sulfides.

16. The method of claim 1, wherein said encapsulant is glass oxide (SiOx).

17. The method of claim 1, wherein said molecule is a biomolecule.

18. The method of claim 17 wherein said biomolecule is a nucleic acid.

19. The method of claim 17 wherein said biomolecule is a protein.

20. A method of encoding the reaction history of a solid support, said method comprising the steps of (a) reacting said solid support with a first reagent under a first reaction condition;

(b) attaching to said solid support a first species of particle comprising a surface-enhanced Raman spectroscopy (SERS)-active metal nanoparticle associated with a first Raman spectroscopy-active molecule and an encapsulant surrounding said SERS-active metal nanoparticle and said Raman spectroscopy-active molecule, wherein said first species of particle has a measurable and distinct SERS spectrum, and wherein said first species of particle encodes the first reagent or the first reaction condition;

(c) reacting said solid support with a second reagent under a second reaction condition; and (d) attaching to said solid support a second species of particle comprising a SERS-active metal nanoparticle associated with a second Raman spectroscopy-active molecule and an encapsulant surrounding said SERS-active metal nanoparticle and said Raman spectroscopy-active molecule, said second species of particle encoding the second reagent or the second reagent condition, wherein said second species of particle has a measurable and distinct SERS spectrum, and said second species of particle having a different spectrum than said first species of particle;

whereby a compound is synthesized on said solid support.

21. A method for conducting an assay comprising:

attaching to a molecule a particle comprising a surface-enhanced Raman spectroscopy (SERS)-active metal nanoparticle associated with a Raman spectroscopy-active molecule and an encapsulant surrounding said SERS-active metal nanoparticle and said Raman spectroscopy-active molecule, wherein said particle has a measurable SERS spectrum; and measuring the SERS spectrum of said assay to determine the presence of said molecule.

22. The method of claim 1, further comprising detecting a SERS spectrum of said particle.

23. The method of claim 20, further comprising detecting a SERS spectrum of said solid support.

24. The method of claim 21, further comprising attaching to a second molecule a second particle comprising a second surface-enhanced Raman spectroscopy (SERS)-active metal nanoparticle associated with a second Raman spectroscopy-active molecule and a second encapsulant surrounding said SERS-active metal nanoparticle and said Raman spectroscopy-active molecule, wherein said second particle has a measurable and distinct SERS spectrum; wherein step (b) further comprises measuring the SERS spectrum of said assay to determine the presence of said second molecule.

* * * * *